United States Patent [19]

Gluchowski et al.

[11] Patent Number: 5,780,485
[45] Date of Patent: *Jul. 14, 1998

[54] USE OF $\alpha_{1C}$ SPECIFIC COMPOUNDS TO TREAT BENIGN PROSTATIC HYPERPLASIA

[75] Inventors: Charles Gluchowski, Wayne; Carlos C. Forray, Waldwick; George Chiu, Bridgewater; Theresa A. Branchek, Teaneck; John M. Wetzel, Elmwood Park; Paul R. Hartig, Princeton, all of N.J.

[73] Assignee: Synaptic Pharmaceutical Corporation, Paramus, N.J.

[ * ] Notice: The term of this patent shall not extend beyond the expiration date of Pat. No. 5,403,847.

[21] Appl. No.: 415,681

[22] Filed: Apr. 3, 1995

Related U.S. Application Data

[63] Continuation of Ser. No. 975,867, Nov. 13, 1992, Pat. No. 5,403,847.

[51] Int. Cl.$^6$ ...................... A61K 31/445; A61K 31/135
[52] U.S. Cl. ............................................. 514/318; 514/654
[58] Field of Search ...................................... 514/318, 654

[56] References Cited

U.S. PATENT DOCUMENTS

| | | | |
|---|---|---|---|
| 4,975,440 | 12/1990 | Flockerzi et al. | |
| 4,994,461 | 2/1991 | Ulrich | |
| 5,403,847 | 4/1995 | Gluchowski et al. | 514/318 |
| 5,508,306 | 4/1996 | Chiu et al. | 514/524 |

FOREIGN PATENT DOCUMENTS

| | | |
|---|---|---|
| 0176956 | 4/1986 | European Pat. Off. |
| 3709796 | 11/1987 | Germany |
| WO9118599 | 12/1991 | WIPO |
| WO9421660 | 9/1994 | WIPO |

OTHER PUBLICATIONS

Forray, C., et al. "The $\alpha_{1C}$-Adrenergic Receptor that Mediates Smooth Muscle Contraction in Human Prostate Has the Pharmacological Properties of the Cloned Human $\alpha_{1C}$Subtype." *Molecular Pharmacology*, 45, 703–708 (1994); U.S.A. (Exhibit 3).

Forray, C., Chiu, G., et al. Effects of Novel Alpha–1C Adrenergic Receptor Antagonists on the Contraction of Human Prostate Smooth Muscle, American Urological Association Eighty–Ninth Annual Meeting, May 14–19, 1994, *The Journal of Urology*, 151(5), Abstract #159 (May 1994); U.S.A. (Exhibit 4).

Forray, C., Bard, J.A., et al. "Comparison of the Pharmacological Properties of the Cloned Bovine, Human, and Rat $\alpha_{1C}$–Adrenergic Receptors." *The FASEB Journal*, 8(4), Abstract #2042 (1994) U.S.A. (Exhibit 5).

Gong, G., et al. $\alpha_{1C}$–Adrenergic Antagonists and Orthostatic Hypotension in the Rat. *The FASEB Journal*, 8(4), Abstract #2043 (1994); U.S.A. (Exhibit 6).

Lepor, H., et al. "Localization of Alpha$_{1C}$ Adrenoceptor ($\alpha_{1C}$AR) Subtypes in the Human Prostate." American Urological Association Eighty–Ninth Annual Meeting, May 14–19, 1994, *The Journal of Urology*, 151(5), Abstract #614 (May 1994); U.S.A. (Exhibit 7).

Perez, J.–L., et al. "Is the $\alpha_{1C}$–Adrenergic Receptor the $\alpha_{1A}$–Subtype?" *The FASEB Journal*, 8(4), Abstract #2041 (1994); U.S.A. (Exhibit 8).

Tang, R., et al. "Localization of Alpha 1C Adrenoceptor ($\alpha_{1C}$ AR) Subtypes in the Human Prostatic Tissue." *The FASEB Journal*, 8 (5), Abstract #5070 (1994); U.S.A. (Exhibit 9).

Wetzel, J.M., et al. "Structural and Functional Studies of the Human $\alpha_{1C}$ Adrenergic Receptor: The Orientation of Transmembrane Helix 5." *The FASEB Journal*, 8(4), Abstract #2182 (1994); U.S.A. (Exhibit 10).

Archibald, J.L. et al., "Antihypertensive Ureidopiperidines," Journal of Medicinal Chemistry (1980), vol. 23, pp. 857–861.

Boer, R. et al., "(+)–Niguldipine binds with very high affinity to $Ca^{2+}$ channels and to a subtype of $\alpha_1$–adrenoreceptors," European Journal of Pharmacology—Molecular Pharmacology Section (1989), vol. 172, pp. 131–145.

Gup, D.I. et al., "Autonomic Receptors in Human Prostate Adenomas," Journal of Urology (1990), vol. 143, pp. 179–185.

Hieble, J.P. et al., "In vitro characterization of the $\alpha_1$–adrenoreceptors in human prostate," European Journal of Pharmacology (1985), vol. 107, pp. 111–117.

Lepor, H. and Baumann, M. et al., Medline Abstracts (1988), Abst. No. 88317114, "The Alpha Adrenergic Binding Properties of Terazosin in the Human Prostate Adenoma and Canine Brain," Journal of Urology (1988), vol. 140(3), pp. 668–671.

Lepor, H. and Knapp–Maloney, G. et al., "A Dose Titration Study Evaluating Terazosin, A Selective, Once–A–Day $\alpha 1$–Blocker for the Treatment of Symptomatic Benign Prostatic Hyperplasia," Journal of Urology (1990), vol. 144, pp. 1393–1398.

Lepor, H. and Shapiro, E. et al., Medline Abstracts (1988), Abst. No. 88317113, "The Effect of Electrocautery on Neurotransmitter Receptor Binding Assays in the Canine Prostate," Journal of Urology (1988), vol. 140(3), pp. 664–667.

(List continued on next page.)

*Primary Examiner*—Keith MacMillan
*Attorney, Agent, or Firm*—John P. White; Cooper & Dunham LLP

[57] ABSTRACT

A method of treating benign prostatic hyperplasia in a subject which comprises administering to the subject a therapeutically effective amount of a compound which binds to a human $\alpha_{1C}$ adrenergic receptor with a binding affinity greater than ten-fold higher than the binding affinity with which the compound binds to a human $\alpha_{1A}$ adrenergic receptor, a human $\alpha_{1B}$ adrenergic receptor, and a human histamine $H_1$ receptor, and, binds to a human $\alpha_2$ adrenergic receptor with a binding affinity which is greater than ten-fold lower than the binding affinity with which the compound binds to such $\alpha_{1C}$ adrenergic receptor. Compounds meeting these criteria are provided.

56 Claims, 2 Drawing Sheets

OTHER PUBLICATIONS

Lomasney, J.W. et al., "Molecular Cloning and Expression of the cDNA for the $\alpha_{1A}$-Adrenergic Receptor," Journal of Biological Chemistry (1991), vol. 266, pp. 6365–6369.

Marshall, I. et al., "Human Alpha$_{1C}$-Adrenoceptor: Functional Characterization In Prostate," Meeting of the British Pharmacological Society (1992), Abst. No. C97.

Ramarao, C.S. et al., "Genomic Organization and Expression of the Human $\alpha_{1B}$-Adrenergic Receptor," Journal of Biological Chemistry (1992), vol. 267, pp. 21936–21944.

Yamada, S. et al., "$\alpha_{1A}$-Adrenergic Receptors in Human Prostate: Characterization and Alteration in Benign Prostatic Hypertrophy," Journal of Pharmacology and Experimental Therapeutics (1987), vol. 242, pp. 326–330.

Chemical Abstracts and 1988:563185, Kaminka et al, 1988.

Chemical Abstracts and 1987:513718, Yamada et al, 1987.

5,780,485

USE OF $\alpha_{1C}$ SPECIFIC COMPOUNDS TO TREAT BENIGN PROSTATIC HYPERPLASIA This is a continuation of application Ser. No. 07/975,867, filed Nov. 13, 1992, now U.S. Pat. No. 5,403,847.

BACKGROUND OF THE INVENTION

Benign Prostatic Hyperplasia (BPH), also called Benign Prostatic Hypertrophy, is a progressive condition which is characterized by a nodular enlargement of prostatic tissue resulting in obstruction of the urethra. This results in increased frequency of urination, nocturia, a poor urine stream and hesitancy or delay in starting the urine flow. Chronic consequences of BPH can include hypertrophy of bladder smooth muscle, a decompensated bladder and an increased incidence of urinary tract infection. The specific biochemical, histological and pharmacological properties of the prostate adenoma leading to the bladder outlet obstruction are not yet known. However, the development of BPH is considered to be an inescapable phenomenon for the aging male population. BPH is observed in approximately 70% of males over the age of 70. Currently, in the United States, the method of choice for treating BPH is surgery (Lepor, H., Urol. Clinics North Amer., 17, 651 (1990)). Over 400,000 prostatectomies are performed annually (data from 1986). A medicinal alternative to surgery is clearly very desirable. The limitations of surgery for treating BPH include the morbidity rate of an operative procedure in elderly men, persistence or recurrence of obstructive and irritative symptoms, as well as the significant cost of surgery.

α-Adrenergic receptors are specific neuroreceptor proteins located in the peripheral and central nervous systems on tissues throughout the body. These receptors are important switches for controlling many physiological functions and, thus, represent important targets for drug development. In fact, many α-adrenergic drugs have been developed over the past 40 years. Examples include clonidine, phenoxybenzamine and prazosin (treatment of hypertension), naphazoline (nasal decongestant), and apraclonidine (treating glaucoma). α-Adrenergic drugs can be broken down into two distinct classes: agonists (clonidine and naphazoline are agonists), which mimic the receptor activation properties of the endogenous neurotransmitter norepinephrine, and antagonists (phenoxybenzamine and prazosin are antagonists), which act to block the effects of norepinephrine. Many of these drugs are effective but also produce unwanted side effects (for example, clonidine produces dry mouth and sedation in addition to its antihypertensive effects).

During the past 15 years a more precise understanding of α-adrenergic receptors and their drugs has evolved through increased scientific scrutiny. Prior to 1977, only one α-adrenergic receptor was known to exist. Between 1977 and 1988, it was accepted by the scientific community that at least two α-adretergic receptors—$\alpha_1$ and $\alpha_2$—existed in the central and peripheral nervous systems. Since 1988, new techniques in molecular biology have led to the identification of at least six α-adrenergic receptors which exist throughout the central and peripheral nervous systems: $\alpha_{1A}$, $\alpha_{1B}$, $\alpha_{1C}$, $\alpha_{2A}$, $\alpha_{2B}$ and $\alpha_{2C}$ (Bylund, D. B., FASEB J., 6, 832 (1992)). It is not known precisely which physiological responses in the body are controlled by each of these receptors. In addition, many α-adrenergic drugs that were developed before 1992 are not selective for any particular α-adrenergic receptor. Many of these drugs produce untoward side effects which may be attributed to their poor α-adrenergic receptor selectivity.

Since the mid 1970's, nonselective α-antagonists have been prescribed to treat BPH. In 1976, M. Caine, et al. (Brit. J. Urol., 48, 255 (1976)), reported that the nonselective α-antagonist phenoxybenzamine was useful in relieving the symptoms of BPH. This drug may produce its effects by interacting with α-receptors located on the prostate. However, this drug also produces significant side effects which severely limit its use in treating patients on a chronic basis. More recently, the α-adrenergic antagonists prazosin and terazosin have also been found to be useful for treating BPH. However, these drugs also produce untoward side effects. The most recently approved drug Proscar™ (Merck) prescribed for BPH is not an α-adrenergic antagonist, but rather acts by blocking 5-α-reductase. While Proscar is able to relieve symptoms, it is effective in only 30% of all patients, and requires a period of up to 6 months to show results.

From binding studies using cloned rat $\alpha_{1A}$, hamster $\alpha_{1B}$, and bovine $\alpha_{1C}$ receptors, and functional studies of antagonism in vitro using human prostrate, I. Marshall, et al., concluded that the receptor mediating contraction of the human prostrate is of the $\alpha_{1C}$ subtype (Marshall, I., et al., Brit. Pharmacol. Soc., (1992)).

Furthermore, using cloned human receptors the binding characteristics of the known BPH drugs to various receptor subtypes have been determined, as described more fully hereinafter. Based upon such binding information and additional data, it has been observed that the side effects which occur with the drugs prazosin and terazosin may be due to their poor selectivity for specific α-adrenergic receptors. In contrast, indoramin is a drug which is slightly selective for the human $\alpha_{1C}$ receptor relative to the other human α-adrenergic receptors, but it also interacts at human histamine H1 receptors. This compound produces untoward side effects which may be attributed to its activity at such $H_1$ receptors.

It would be desirable to provide methods and compounds which allow the treatment of BPH but which avoid the production of side effects observed for all currently used medications.

From the binding information described hereinafter, it has unexpectedly been discovered that compounds which are specific for an $\alpha_{1C}$ adrenergic receptor with a binding affinity greater than ten-fold higher than the binding affinity with which the compounds bind to an $\alpha_{1A}$ adrenergic receptor, a human $\alpha_{1B}$ adrenergic receptor, and a human histamine $H_1$ receptor, and (b) bind to an $\alpha_2$ adrenergic receptor with a binding affinity which is greater than ten-fold lower than the binding affinity with which the compounds bind to such $\alpha_{1C}$ adrenergic receptor are effective for the treatment of BPH.

BRIEF DESCRIPTION OF THE DRAWINGS

A more complete understanding of the invention and many of its advantages will become apparent by reference to the detailed description which follows when considered in conjunction with the accompanying drawings, wherein.

SUMMARY OF THE INVENTION

Figure 1:
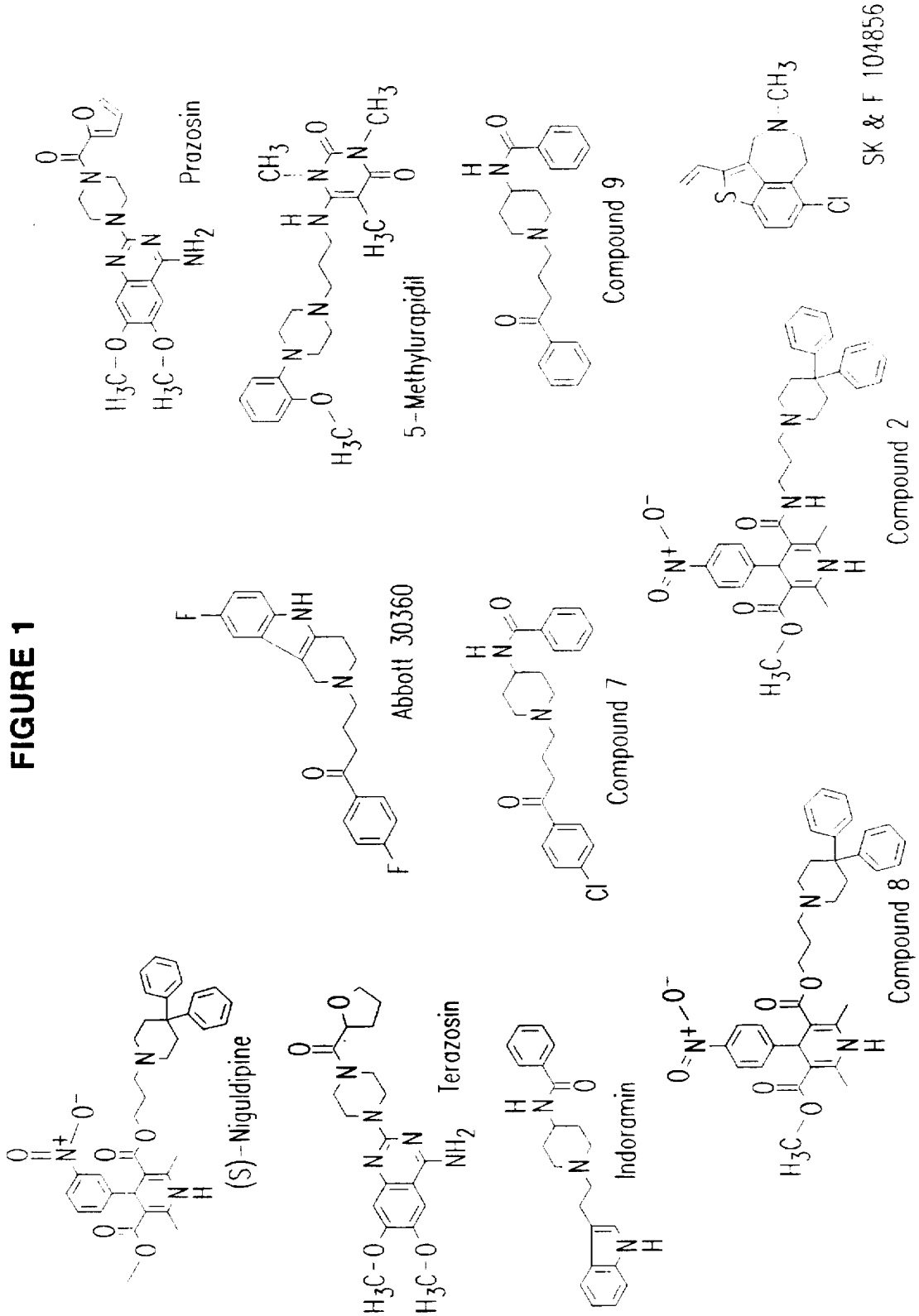
FIG. 1 illustrates compounds which are potent antagonists of the cloned human $\alpha_{1C}$ receptor.

The present invention provides a method of treating benign prostatic hyperplasia in a subject which comprises administering to the subject a therapeutically effective amount of a compound which (a) binds to a human $\alpha_{1C}$ adrenergic receptor with a binding affinity greater than ten-fold higher than the binding affinity with which the compound binds to a human $\alpha_{1A}$ adrenergic receptor, a human $\alpha_{1B}$ adrenergic receptor, and a human histamine $H_1$ receptor, and (b) binds to a human $\alpha_2$ adrenergic receptor with a binding affinity which is greater than ten-fold lower than the binding affinity with which the compound binds to such $\alpha_{1C}$ adrenergic receptor.

The present invention also provides a method of inhibiting contraction of prostate tissue which comprises contacting the prostate tissue with an effective contraction-inhibiting amount of a compound which (a) binds to a human $\alpha_{1C}$ adrenergic receptor with a binding affinity greater than ten-fold higher than the binding affinity with which the compound binds to a human $\alpha_{1A}$ adrenergic receptor, a human $\alpha_{1B}$ adrenergic receptor, and a human histamine $H_1$ receptor, and (b) binds to a human $\alpha_2$ adrenergic receptor with a binding affinity which is greater than ten-fold lower than the binding affinity with which the compound binds to such $\alpha_{1C}$ adrenergic receptor.

DETAILED DESCRIPTION OF THE INVENTION

The present invention provides a method of treating benign prostatic hyperplasia in a subject which comprises administering to the subject a therapeutically effective amount of a compound which (a) binds to a human $\alpha_{1C}$ adrenergic receptor with a binding affinity greater than ten-fold higher than the binding affinity with which the compound binds to a human $\alpha_{1A}$ adrenergic receptor, a human $\alpha_{1B}$ adrenergic receptor, and a human histamine $H_1$ receptor, and (b) binds to a human $\alpha_2$ adrenergic receptor with a binding affinity which is greater than ten-fold lower than the binding affinity with which the compound binds to such $\alpha_{1C}$ adrenergic receptor.

Desirably, the compound used to practice the method of the invention additionally binds to a calcium channel with a binding affinity which is greater than ten-fold lower than the binding affinity with which the compound binds to the $\alpha_{1C}$ adrenergic receptor.

Alternatively or incrementally, the compound used to practice the method of the invention also binds to a human dopamine $D_2$ receptor with a binding affinity which is greater than ten-fold lower than the binding affinity with which the compound binds to the $\alpha_{1C}$ adrenergic receptor.

Alternatively or incrementally, the compound used to practice the method of the invention additionally birds to a human histamine H2 receptor with a binding affinity which is greater than ten-fold lower than the binding affinity with which the compound binds to the $\alpha_{1C}$ adrenergic receptor.

Alternatively or incrementally, the compound used to practice the method of the invention additionally binds to any serotonin receptor with a binding affinity which is greater than ten-fold lower than the binding affinity with which the compound binds to the $\alpha_{1C}$ adrenergic receptor.

Alternatively or incrementally, the compound used to practice the method of the invention also binds to a human dopamine $D_3$ receptor with a binding affinity which is greater than ten-fold lower than the binding affinity with which the compound binds to the $\alpha_{1C}$ adrenergic receptor.

Alternatively or incrementally, the compound used to practice the method of the invention also binds to a human dopamine $D_4$ with a binding affinity which is greater than ten-fold lower than the binding affinity with which the compound binds to the $\alpha_{1C}$ adrenergic receptor.

Alternatively or incrementally, the compound used to practice the method of the invention also binds to a human dopamine $D_5$ receptor with a binding affinity which is greater than ten-fold lower than the binding affinity with which the compound binds to the $\alpha_{1C}$ adrenergic receptor.

A number of compounds have been identified or synthesized which are useful in the practice of the invention. For example, the compound has the structure:

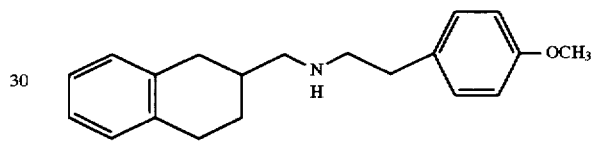

In another example, the compound has the structure:

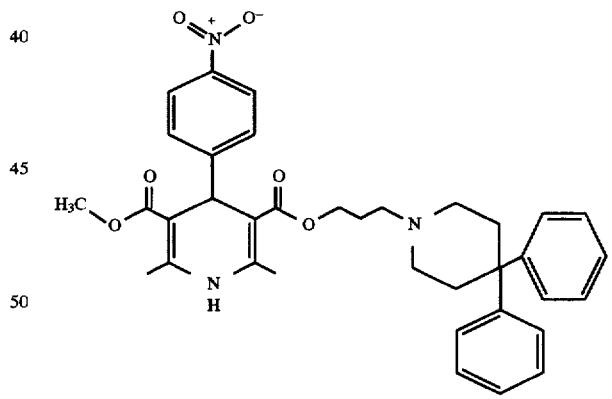

In still another example, the compound has the structure:

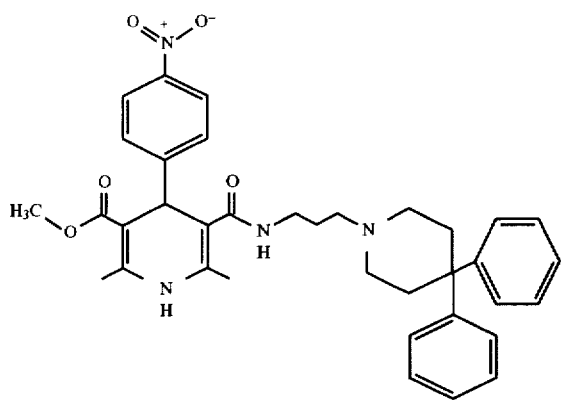

In an additional example, the compound has the structure:

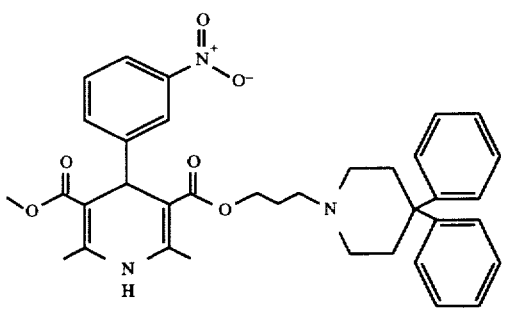

Included within the scope of the method of treating BPH in accord with the invention are the use of both R and S enantiomers of the compounds described which possess stereogenic centers, as well as the use of pharmaceutically acceptable salts and complexes thereof.

The invention also provides a method of inhibiting contraction of prostate tissue which comprises contacting the prostate tissue with an effective contraction-inhibiting amount of a compound which (a) binds to a human $\alpha_{1C}$ adrenergic receptor with a binding affinity greater than ten-fold higher than the binding affinity with which the compound binds to a human $\alpha_{1A}$ adrenergic receptor, a human $\alpha_{1B}$ adrenergic receptor, and a human histamine $H_1$ receptor, and (b) binds to a human $\alpha_2$ adrenergic receptor with a binding affinity which is greater than ten-fold lower than the binding affinity with which the compound binds to such $\alpha_{1C}$ adrenergic receptor.

The activity of compounds at the different human receptors was determined in vitro using cultured cell lines that selectively express the receptor of interest. These cell lines were prepared by transfecting the cloned cDNA or cloned genomic DNA or constructs containing both genomic DNA and CDNA encoding the human α-adrenergic, serotonin, histamine, and dopamine receptors as further described in detail in Example 9 hereinbelow.

In connection with this invention, a number of cloned human receptors discussed herein, either as plasmids or as stably transfected cell lines, have been made pursuant to, and in satisfaction of, the Budapest Treaty on the International Recognition of the Deposit of Micro-organisms for the Purpose of Patent Procedure, and are made with the American Type Culture Collection, 12301 Parklawn Drive, Rockville, Md. 20852. Specifically, these deposits have been accorded ATCC Accession Numbers as follows:

| Designation | ATCC Accession No. | Date |
|---|---|---|
| L-$\alpha_{1A}$ | CRL 11138 | September 25, 1992 |
| L-$\alpha_{1B}$ | CRL 11139 | September 25, 1992 |
| L-$\alpha_{1C}$ | CRL 11140 | September 25, 1992 |
| L-$\alpha_{2A}$ | CRL 11180 | November 6, 1992 |
| L-NGC-$\alpha_{2B}$ | CRL 10275 | October 25, 1989 |
| L-$\alpha_{2C}$ | CRL 11181 | November 6, 1992 |
| pcEXV-H$_1$ | ATCC 75346 | November 6, 1992 |
| pcEXV-H$_2$ | ATCC 75345 | November 6, 1992 |
| pcEXV-D$_2$ | ATCC 75344 | November 6, 1992 |

The data shown in the accompanying Tables 1 and 2 indicate that the $\alpha_{1C}$-specific receptor antagonists which satisfy the criteria as defined herein have significant efficacy in the inhibition of contraction of human prostate tissue. This in vitro property is recognized in the art as correlating with efficacy in treating benign prostatic hyperplasia in vivo.

The present invention therefore provides a method of treating benign prostatic hyperplasia, which comprises administering a quantity of any of the $\alpha_{1C}$ receptor antagonists defined as herein in a quantity effective against BPH. The drug may be administered to a patient afflicted with benign prostatic hyperplasia by any conventional route of administration, including, but not limited to, intravenous, intramuscular, oral, subcutaneous, intratumoral, intradermal, and parenteral. The quantity effective against BPH is between 0.001 mg and 10.0 mg per kg of subject body weight.

The method of treating BPH disclosed in the present invention may also be carried out using a pharmaceutical composition comprising any of the $\alpha_{1C}$ receptor antagonists as defined herein and a pharmaceutically acceptable carrier. The composition may contain between 0.05 mg and 500 mg of an $\alpha_{1C}$ receptor antagonist, and may be constituted into any form suitable for the mode of administration selected. Compositions suitable for oral administration include solid forms, such as pills, capsules, granules, tablets, and powders, and liquid forms, such as solutions, syrups, elixers, and suspensions. Forms useful for parenteral administration include sterile solutions, emulsions, and suspensions.

The drug may otherwise be prepared as a sterile solid composition which may be dissolved or suspended at the time of administration using sterile water, saline, or other appropriate sterile injectable medium. Carriers are intended to include necessary and inert binders, suspending agents, lubricants, flavorants, sweeteners, preservatives, dyes, and coatings.

Optimal dosages to be administered may be readily determined by those skilled in the art, and will vary with the particular $\alpha_{1C}$ receptor antagonist in use, the strength of the preparation, the mode of administration, and the advancement of the disease condition. Additional factors depending on the particular patient being treated will result in a need to adjust dosages, including patient age, weight, diet, and time of administration.

The following Experimental Details are set forth to aid in an understanding of the invention, and are not intended, and should not be construed, to limit in any way the invention set forth in the claims which follow thereafter.

Experimental Details

Prazosin, 5-methylurapidil, and S-niguldipine were obtained from Research Biochemicals, Inc. A30360 (4-fluoro-4-(8-fluoro-1,3,4,5-tetrahydro-2H-pyrido[4,3-b] indol-2-yl)butyrophenone hydrochloride) was obtained

EXAMPLE 1
Synthesis of Terazosin Hydrochloride
N-(2-Furoyl)piperazine

This compound and its preparation has been described in Great Britain Patents 1,390,014 and 1,390,015. Piperazine hexahydrate (194 g, 1 mole) was dissolved in 250 ml $H_2O$. The solution was acidified to pH 4.5 with 6N HCl. Furoyl chloride (130.5 g, 1 mole, Aldrich) was added along with 10% NaOH solution at such a rate that the pH was maintained at 4.5. After 1 hour, the solution was made basic (pH=8.5) with NaOH solution. The reaction mixture was continuously extracted with chloroform for 36 hours. The $CHCl_3$ extract was dried over $MgSO_4$, and filtered. Distillation gave 108.2 g product (60%), b.p. 132°–138° C./0.6 mm Hg, m.p. 69°–70° C.

N-(Tetrahydro-2-furoyl)piperazine

The furoylpiperazine of Example 1 was converted to the hydrobromide salt (m.p. 173°–175° C.). This salt (39.0 g) in 250 ml methyl alcohol and 9.0 g Raney nickel was hydrogenated at 3 atm. After uptake of $H_2$ ceased, the catalyst was filtered, the solvent concentrated, and the residue crystallized from isopropyl alcohol to give 35.2 g. tetrahydrofuroylpiperazine HBr, m.p. 152°–156° C. This was suspended in 20 ml $H_2O$. Then 10.5 g 50%. NaOH solution was added slowly followed by 2.0 g solid $Na_2CO_3$. This was extracted with 4×100 ml portions of warm $CHCl_3$. The $CHCl_3$ extractions were distilled to give 22.5 g tetrahydrofurolylpiperazine, b.p. 120°–125° C./0.2 mm Hg.

2[4-(Tetrahydro-2-furoyl)piperazinyl]-4-amino-6,7-dimethoxyquinazoline hydrochloride To 7.00 g 2-chloro-4-amino-6,7-dimethoxyquinazoline (Lancaster Synthesis) in 50 ml methoxyethanol was added 10.8 g. tetrahydrofurolylpiperazine, and the mixture refluxed 3 hours. The clear solution was concentrated and an aqueous solution of potassium bicarbonate was added. The resultant solid that formed was filtered and washed with water. It was then added to methanol and the resulting suspension was acidified with a solution of hydrogen chloride in isopropyl alcohol. The resulting solution was concentrated and the residue crystallized from isopropyl alcohol giving 8.12 g. of product, m.p. 278°–279° C.

EXAMPLE 2
Preparation of Indoramin
4-Benzamido-1-[2-(3-indolyl)ethylpyridinium Bromide A solution of 4-benzamidopyridine (1.98 g) and 3-(2-bromoethyl)indole (2.24 g) in EtOH (15 ml) was refluxed for 2 hours, and the crystallized product (3.13 g, mp 264°–266° C.) was collected by filtration from the hot reaction mixture. Recyrstallization gave the hydrate 3-[2-4-Benzamidoperid-1-yl)ethyl]indole (Indoramin)

4-Benzamido-1-[2-(3-indolyl)ethyl]pyridinium bromide (3.0 g) in 91% EtOH (300 ml) containing $Et_3N$ (0.8 g) was hydrogenated in the presence of freshly prepared W-7 Raney Ni catalyst (ca. 3 g) at 28.12 kg/cm² and 50° for 4 hours. After filtering off the catalyst, the filtrate was evaporated and the residue was shaken with $CHCl_3$ and 2N NaOH. The resulting insoluble material (1.61 g, mp 203°–206° C.) was collected and dried. Recrystallization from EtOH gave the product (1.34 g), as colorless needles.

EXAMPLE 3
Preparation of 1-(3-benzoylpropyl)-4-benzamidopiperidine (Commpound 9)

A mixture of 4-chlorobutyrophenone (447 mg, 2.45 mmol), 4-benzamidopiperidine (500 mg, 2.45 mmol) and $K_2CO_3$ (338 mg, 2.45 mmol) was heated up in boiling water bath for 1 hour. The reaction mixture was portioned between water and $CHCl_3$. The organic layer was separated and dried over $Na_2SO_4$. After filtration and removal of solvent, the residue was purified by chromatography ($SiO_2$, MeOH:$CHCl_3$, 5:95). Recrystallization from AcOEt/hexane gave a white powder (78 mg, 8.2%), mp 143°–144° O.C; $^1$H NMR ($CD_3OD$, 400 MHz) δ 1.65 (dq, $J_1$=3.16 Hz, $J_2$=11.9 Hz, 2H), 1.90–2.00 (m, 4H), 2.18 (t, J=11.9 Hz, 2H), 2.48 (m, 2H), 3.00–3.10 (m, 4H), 3.88 (m, 1H), 7.40–8.00 (m, 10H); Mass spectrum $(M+1)^+$ at m/z 351.

EXAMPLE 4
Preparation of 1-[3-(4-chlorobenzoyl)propyl]-4-benzamidopiperidine (Compound 7)

A mixture of 3-(4-chlorobenzol)propyl bromide (640 mg, 2.45 mmol), 4-benzamidopiperidine (500 mg, 2.45 mmol) and $K_2CO_3$ (1.01 g, 7.34 mmol) in 50 ml of acetone was heated up to refluxing condition for 48 hours. The solid was removed by filtration. Concentration of filtrate in vacuo gave a yellowish solid, which was purified by chromatography ($SiO_2$, MeOH:$CHCl_3$, 5:95). 320 mg (33.9%) of white powder was obtained $^1$H NMR ($CDCl_3$, 300 mHz) δ 1.46 (dq, $J_1$=1.0 Hz, $J_2$=8.4 Hz, 2H), 1.90–2.10 (m, 4H), 2.16 (m, 2H), 2.43 (t, J=6.9 Hz, 2H), 2.80–2.90 (m, 2H), 2.97 (t, J=6.9 Hz, 2H), 3.97 (m, 1H), 5.92 (d, J=7.8 Hz, 1H, N-H), 7.40–8.00 (m, 9H); Product was converted to HCl salt and recrystallized with MeOH/$Et_2O$, mp 243°–244° C.; Calcd for $C_{22}H_{25}ClN_2I_2$ HCl.$H_2O$: C 60.15, H 6.37, N 6.37; Found: C 60.18, H 6.34, N 6.29.

EXAMPLE 5
Preparation of SKF-104856
1-[(4-Chlorophenyl)thio]-2-propanone

Chloroacetone (32.3 g, 0.347 mol) was added to a mixture of 4-chlorothiophenol (50 g, 0.347 mmol) and sodium hydroxide (14 g, 0.347 mol) in water (400 ml) and the mixture was stirred at 25° C. for 1 hour. The mixture was extracted with ethyl ether and the organic phase was washed with water, dried with magnesium sulfate and concentrated to give 69 g (99%) of 1-[(4-chlorophenyl)thio]-2-propanone.

5-Chloro-3-methylbenzo(b)thiophene

1-[(4-Cholorophenyl)thio]-2-propanone (50 g, 0.25 mol) was added to polyphosphoric acid (300 g) and the mixture was stirred as the temperature was gradually raised to 120° C. as an exotherm started. The mixture was stirred at 130° C. for 1 hour, diluted with water, extracted with ethyl ether and the organic phase was dried and concentrated. The residue was stirred in methanol (200 ml), filtered and the filtrate concentrated to give 17.5 g (40%) of 5-chloro-3-methylbenzo(b)thiophene: bp 120° C. (0.6 mm Hg).

Ethyl 5-chloro-3-methylbenzo(b)thiophene-2-carboxylate n-Butyllithium in hexane (2.6M, 2.3 ml) was added to a solution of 5-chloro-3-methylbenzo(b)thiophene (1.0 g, 6 mmol) in ethyl ether (20 ml) stirred at 0° C. under argon. The mixture was stirred for 30 minutes and transferred slowly under argon pressure to a stirred solution of ethyl chloroformate (0.63 g, 6 mmol) in ethyl ether (20 ml). The mixture was stirred at 0° C. for 30 minutes and at 25° C. for 1.5 hours. The mixture was treated with water and the organic phase was dried, concentrated and triturated with hexane to give 1.0 g (67%) of ethyl 5-chloro-3-methylbenzo(b)thiophene-2-carboxylate: mp 92.5°–94° C.

Ethyl 3-bromomethyl-5-chlorobenzo(b)thiophene-2-carboxylate

A mixture of ethyl 5-chloro-3-methylbenzo(b)thiophene-2-carboxylate (9.0 g, 0.035 mol), N-bromosuccinimide (6.53 g, 0.037 mol) and benzoyl peroxide (130 mg) in carbon tetrachloride (150 ml) was refluxed and illuminated with sunlamp for 2 hours. The resulting suspension was cooled, filtered and the filter cake was triturated with methanol to give 9.9 g. (85%) of the methanol-insoluble ethyl 3-bromomethyl-5-chlorobenzo(b)thiophene-2-carboxylate: mp 148°–150° C.

Ethyl 5-Chloro-3-|N-(2,2-dimethoxyethyl)-N-methyl (amino-methyl)|benzol(b)thiophene-2-carboxylate A mixture of ethyl 3-bromomethyl-5-chlorobenzo(b)thiophene-2-carboxylate (11 g, 0.033 mol), methylaminoacetaldehyde dimethyl acetal (4.76 g, 0.04 mol) and potassium carbonate (11.4 g, 0.8 mol) in dry acetone (200 ml) was stirred for 48 hours, filtered and the filtrate concentrated to give 11.8 g. (96%) of ethyl 5-chloro-3-(N-2,2-dimethoxyethyl)-N-methyl(aminomethyl)benzol(b)thiophene-2-carboxylate.

Ethyl 7-chloro-3,4-dihydro-4-methylthieno|4,3,2-ef|-|3|benzazepine-2-carboxylate Ethyl 5-chloro-3-[N-(2,2-dimethoxyethyl)-N-methyl (aminomethyl)|benzo|b|thiophene-2-carboxylate (3.0 g, 8.1 mmol) was added in portions to trifluoromethanesulfonic acid (10 ml) stirred at 0° C. under argon. The mixture was stirred at 25° C. for 45 minutes and diluted with water. The mixture was basified with aqueous sodium hydroxide and extracted with ethyl ether to give ethyl 7-chloro-3,4-dihydro-4-methylthieno-|4,3,2-ef||3|benzazepine-2-carboxylate.

Ethyl 7-chloro-3,4,5,6-tetrahydro-4-methylthieno|4,3,2-ef||3|benzazepine-2-carboxylate Diborane in tetrahydrofuaran (1M, 40 ml) was added to a solution of ethyl 7-chloro-3,4-dihydro-4-methylthieno|4,3,2-ef||3|benzazepine-2-carboxylate (2.8 g) in tetrahydrofuran (30 ml) stirred at 0° C. The mixture was refluxed for 3 hours and stirred at 25° C. for 18 hours, cooled, treated with methanol (50 ml), refluxed for 18 hours and concentrated. The residue was triturated with ethyl ether-hexane (3:1) to give 1.6 g (84%) of ethyl 7-chloro-3,4,5,6-tetrahydro-4-methylthieno|4 , 3, 2-ef]|3|benzazepine-2-carboxylate: mp 138°–140° C. The free base was treated with hydrogen chloride to give ethyl 7-chloro-3,4,5,6-tetrahydro-4-methylthieno|4,3,2-ef]|3|benzazepine-2-carboxylate hydrochloride: mp 240° C.

7-Chloro-3,4,5,6-tetrahydro-4-methylthisno [4,3,2-ef]|3] benzazepine-2-methanol

A solution of ethyl 7-chloro-3,4,5,6-tetrahydro-4-methylthieno|4.3.2-ef][3)benzazepine-2-carboxylate (4.0 g, 12.9 mmol), in ethyl ether (48 ml) was treated with lithium aluminum hydride (0.53 g, 14 mmol). The mixture was stirred for 1.5 hours, cooled and treated carefully with water (2.0 ml), 10% sodium hydroxide (1.0 ml) and water (2. 0 ml). The resulting mixture was filtered and the solvent evaporated to give 1.9 g (57%) of 7-chloro-3,4,5,6-tetrahydro-4-methylthieno|4,3,2-ef ]|3|benzazepine-2-methanol: mp 184°–185° C.

7-Chloro-3,4,5,6-tetrahydro-4-methylthieno-4,3,2-ef][3] benzazopine-2-carboxaldehyde A solution of 7-chloro-3,4,5,6-tetrahydro-4-methylthieno |4,3,2-ef||3|benzazepine-2-methanol (1.6 g, 6 mmol) in dichloromethane (150 ml) was stirred under argon with activated manganese dioxide (8.3 g) for 2 hours. The mixture was filtered through Celite™ and the filtrate was dried with magnesium sulfate and concentrated to give a 63% yield of 7-chloro-3,4,5,6-tetrahydro-4-methylthieno|4,3,2-ef||3|benzazepine-2-carboxaldehyde.

7-Chloro-2-ethenyl-3,4,5,6-tetrahdyro-4-methylthieno|4,3, 2-ef||3|benzazepine (SKP-104856)

Sodium hydride (60% dispersion in mineral oil, 3.8 mmol) was added to a stirred solution of methyltriphenyl-phosphonium bromide (1.35 g, 3.8 mmol) in dry tetrahydrofuran (30 ml) and stirred for 15 minutes. The mixture was treated with a solution of 7-chloro-3,4,5,6-tetrahydro-4-methylthieno|4,3,2-ef||3|-benzazepine-2-carboxaldehyde, prepared as in Example 3, (0.5 g, 1.9 mmol) in dimethylformamide (4 ml), stirred at 25° C. for 16 hours, quenched with ice and extracted with ethyl acetate. The organic phase was washed, dried and concentrated and the residue was chromatographed on silica gel eluted with a gradient of methylene chloride to methanol-methylene chloride (3.5:96.5). The product was treated with hydrogen chloride to give 0.2 g (35%) of 7-chloro-2-ethenyl-3,4,5,6-tetrahydro-4-methylthieno|4,3,2-ef||3|benzazepine hydrochloride: mp 234°–236° C.

EXAMPLE 6

2-Hydroxymethyl-1,2,3,4-tetrahydronaphthalene

A solution of 1,2,34-tetrahydro-2-naphthoic acid (2.50 g, 14.2 mmol) in 100 ml THF was treated with LiAlH$_4$ (681 mg, 17.04 mmol) and the reaction mixture was heated at reflux for 5 hours. The suspension was cooled to 0° C. and quenched by addition of solid Na$_2$SO$_4$■10H$_2$O. The mixture was stirred at room temperature for 4 hours. The solid was removed by filtration. Concentration of filtrate in vacuo gave a yellowish oil (2.28 g, 98.8%); $^1$H NMR (CDCl$_3$, 300 MHz) δ 1.43 (m, 1H) , 2.00 (m, 2H) 2.51 (dd, J$_1$=16.5 Hz, J$_2$=10.8 Hz, 1H), 2.85 (m, 3H), 3.65 (dd, J$_1$=6.3 Hz, J$_2$=1.2 Hz, 2H), 7.09 (s, 4H).

2-Bromomethyl-1,2,3,4-tetrahydronaphthalene

A solution of 2-hydroxymethyl-1,2,3,4-tetrahydronaphthalene (2.28 g, 14.0 mmol) in 100 ml of CH$_2$Cl$_2$ was treated with PBr$_3$ (1.28 g, 4.73 mmol) at 0° C. The mixture was stirred at room temperature for 72 hours then poured onto 100 g of ice. The organic layer was isolated, washed with 10% K$_2$CO$_4$ aqueous solution, H$_2$O, sat'd brine, and then dried over Nα$_2$SO$_4$. After filtration and removal of solvent, the residue was purified by chromatography (SiO$_2$, EtOAc:hexane, 1:10) to give a colorless oil (1.33 g, 41.6%); $^1$H NMR (CDCl$_3$, 300 MHz) δ 1.55 (m, 1H), 2.11 (m, 1H), 2.11 (m, 2H), 2.58 (dd, J$_1$=16.2 Hz, J$_2$=10.2 Hz, 1H), 2.80–3.10 (m, 3H), 3.45 (d, J=6.3 Hz, 2H), 7.10 (m, 4H).

2-[(4-Methoxyphenethyl)aminomethyl]-1,2,3,4-tetrahydronaphthalene. (Compound 11)

A solution of 2-bromomethyl-1,2,3,4-tetrahydronaphthalene (1.33 g, 5.91 mmol) and 4-methoxyphenethylamine (1.79 g, 11.8 mmol) in 50 ml of EtOH was refluxed for 48 hours. After removal of EtOH in vacuo, the residue was dissolved in 100 ml of CHCl$_3$, washed with 10% K$_2$CO$_3$, H$_2$O, sat'd brine, and then dried over Na$_2$SO$_4$. Filtration followed by evaporation of solvent gave a yellow oil, which was purified by chromatography (SiO$_2$, MeOH:CHCl$_3$, 5:95) to a give a yellowish oil (1.03 g, 58.9%). The product was converted to HCl salt, crystallization with MeOH/Et$_2$O gave a white powder. mp 274°–275° C.; Calcd for C$_{20}$H$_{25}$NO.HCl: C 72.37, H 7.91, N 4.22; Found C 72.40, H 7.76, N 4.13.

EXAMPLE 7

4,4-Diphenylpiperidine hydrochloride

A mixture of 4-piperidone monohydrate hydrochloride (15.0 g, 97.6 mmol, 1.00 equiv, Aldrich) and AlCl$_3$ (130 g, 976 mmol, 10.0 equiv) in anhydrous benzene (600 mL) was stirred at reflux for 4 hours. Ice (300 g) and water (50 mL) were added, the mixture was filtered, and the solid was washed with toluene and dried to afford 19.2 g (72%) of off-white solid, which was pure by $^1$H NMR. Recrystallization from ethanol gave the analytically pure sample: m.p.

300°–301° C.; ¹H NMR (300 MHz, CD₃OD) δ 2.65 (m, 4 H), 3.18 (m, 4 H), 7.18 (m, 2 H), 7.30 (m, 8 H); Anal. Calcd. for C₁₇H₁₉N.HCl: C, 74.57; H, 7.36; N, 5.12. Found: C, 74.32; H, 7.34; N, 5.02. The free base was generated by addition of the above salt to dilute aqueous sodium hydroxide and extraction with CH₂Cl₂. The organic phase was dried over MgSO₄ and concentrated to give a light brown solid: IR (neat) 2942.8, 1494.5, 1445.9 cm⁻¹; CIMS (NH₃) m/e 238 (M+1)⁺.

3-(4,4-Diphenylpiperidin-1-yl)propionitrile

To a suspension of 4,4-diphenylpiperidine hydrochloride (195 mg, 0.712 mmol, 1.0 equiv) in ETOh (1.5 mL) was added triethylamine (0.25 mL, 1.83 mmol, 2.6 equiv) followed by acrylonitrile (0.13 mL, 2.01 mmol, 2.8 equiv). The resulting solution was stirred at room temperature under argon for 15 minutes and then concentrated. Water was added, and the mixture was extracted three times with EtOAc. The combined organic extracts were dried over MgSO₄ and concentrated to give 170 mg (87%) of tan solid, which was used for the next reaction without purification. m.p. 95°–96° C.; ¹H NMR (300 MHz, CDCl₃) δ 2.37 (m, 2H), 2.46 (m, 4H), 2.52 (m, 6H), 7.12 (m, 2H), 7.23 (m, 8H); ¹³C NMR (75 MHz, CDCl₃) δ 16.65, 36.71, 45.08, 50.78, 54.13, 119.70, 126.48, 127.78, 129.11, 147.87; IR (neat) 2944.4, 2821.0, 1495.5, 1445.9 cm⁻¹.

1-(3-Aminopropyl)-4,4-diphenylpiperidine

To a stirred solution of 3-(4,4-diphenylpiperidine-1-yl) propionitrile (2.00 g, 6.89 mmol, 1.0 equiv) in anhydrous THF (20 mL) under argon was added a solution of BH₃ in THF (1.0M, 24.1 mL, 24 mmol, 3.5 equiv) at room temperature. The mixture was refluxed for 4.5 hours and then cooled to room temperature. Aqueous HCl (6N, 50 mL) was added and stirring was continued for 1 hour. The mixture was basified to pH 9 by addition of 6N aq. NaOH, extracted 3 times with CH₂Cl₂, dried over MgSO₄ and concentrated. The residue was purified by flash chromatography (SiO₂, EtOAc-MeOH, 9:1, followed by EtOAc-MeOH-isopropylamine (60:10:1), followed by EtOAc-MeOH-isopropylamine (40:10:2) to give 1.35 g (66%) of tan solid: m.p. 98°–99° C.; ¹H NMR (300 MHz, CDCl₃) δ 1.64 (tt, J=7.7 Hz, 2H), 2.33 (br t, J=7.2 Hz, 2H), 2.50 (m, 8H), 2.76 (br t, J=6.5 Hz, 2H), 3.06 (br s, 2H), 7.13 (m, 2H), 7.26 (m, 8H); ¹³C NMR (75 MHz, CDCl₃) δ 29.79, 36.80, 41.41, 45.24, 51.25, 57.41, 126.30, 127.77, 128.97, 148.11; IR (neat) 3361.5 cm⁻¹; CIMS (NH₃) m/e 295 (M+1)⁺.

Acetoacetic acid N-[3-(4,4-diphenylpiperidin-1-yl)propyl] amide

Diketene (0.44 mL, 5.68 mmol, 1.3 equiv, Aldrich) was added at room temperature to a stirred solution of 1-(3-aminopropyl)-4,4-diphenylpiperidine (1.288 g, 4.37 mmol, 1.0 equiv) in anhydrous toluene (15 mL) under argon, and stirring was continued for 48 hours. The mixture was concentrated to give 1.294 g (78%) of white solid, which was used for the next reaction without purification: ¹H NMR (300 MHz, CDCl₃) δ 1.70 (tt, J=6.4, 6.4 Hz, 2H), 2.23 (s, 3H), 2.44 (br t, J=6.5 Hz), 2.49–2.67 (m, 8H), 3.32 (br t, J=5.8 Hz), 3.36 (s, 2H), 7.16 (m, 2H), 7.27 (m, 8H).

2,6-Dimethyl-4-(4-nitrophenyl)-1,4-dihydropyridine-3,5-dicarboxylic acid N-[3-(4,4-diphenylpiperidine-1-yl)propyl] amide methyl ester A solution of acetoacetic acid N-[3-(4,4-diphenylpiperidin-1-yl)propyl]amide (365 mg, 0.964 mmol, 1.0 equiv), methyl 3-aminocrotonate (138 mg, 1.20 mmol, 1.2 equiv, Aldrich), and 4-nitrobenzaldehyde (181 mg, 1.20 mmol, 1.2 equiv, Aldrich) in isopropanol was refluxed under argon for 60 hours. The mixture was cooled to room temperature and concentrated, and the residue was diluted with CH₂Cl₂, washed with water, dried over MgSO₄, and concentrated. The residue was purified by flash chromatography (SiO₂, EtOAc, followed by EtOAc-MeOH, 19:1 and 9:1) to give 147.8 mg (25%) of yellow solid: ¹H NMR (300 MHz, CDCl₃) δ 1.55 (m, 2H), 2.14 (s, 3H), 2.15–2.50 (m, 10H), 2.32 (s, 3H), 3.20 (m, 1H), 3.37 (m, 1H), 3.54 (s, 3H), 5.00 (s, 3H), 5.48 (br s), 6.98 (br t, J=4.9 Hz, 1H), 7.14–7.30 (m, 10H), 7.39 (dm, J=8.7 Hz, 2H), 8.05 (dm, J=8.7 Hz, 2H); ¹³C NMR (75 MHz, CDCl₃) δ 18.74, 20.64, 25.61, 36.77, 40.20, 42.26, 45.03, 51.16, 51.61, 58.08, 100.65, 109.71, 124.35, 126.46, 127.61, 128.84, 129.06, 135.52, 146.96, 147.10, 154.55, 168.22, 168.70; IR (neat) 1680, 1610, 1515, 1340 cm⁻¹; MS (FAB) m/e 609 (M+H)⁺.

2,6-Dimethyl-4-(4-nitrophenyl)-1,4-dihydropyridine-3,5-dicarboxylic acid N-[3-(4,4-diphanylpiperidin-1-yl)-propyl] amide methyl ester hydrochloride hydrate (Compound 2)

To a solution of 2,6-dimethyl-4-(4-nitrophenyl)-1,4-dihydro-pyridine-3,5-dicarboxylic acid N-[3-(4,4-diphenylpiperidin-1-yl)propyl|amide methyl ester (147.8 mg, 0.243 mmol, 1.0 equiv) in EtOH (2 mL) was added a solution of HCl in ether (1.0M, 0.24 mL, 0.24 mmol, 1.0 equiv). Addition of ethyl acetate (3 mL) followed by heating gave a clear solution. Slow cooling of this solution, followed by filtration gave 91 mg of yellow crystalline solid: m.p. 182°–183° C.; Anal. Calcd. for CH₄₀N₄O₅.HCl.H₂O: C, 65.20, H, 6.54; N, 8.45. Found: C, 65.30; H, 6.28; N, 8.15.

EXAMPLE 8

3-(4,4-Diphenylpiperid-1-yl)-propanol 4,4-Diphenylpiperidine (40 g), 3-bromopropanol (24.7 g, Aldrich), powdered potassium carbonate (116.4 g) and approximately 1 g of potassium iodide (in 500 ml of a 1:1 mixture of dioxane and 1-butanol) were heated for about 48 hours under reflux and with vigorous stirring. After cooling, the mixture was filtered, and the filtrate was concentrated. The oily residue was taken up in ethyl acetate, and the solution was filtered again. Concentrating the filtrate to dryness yielded the product in the form of a yellowish, oily residue which slowly solidifies to a wax-like product (yield: 44.8 g). Hydrochloric acid in ether produced the hydrochloride (m.p.: 226° to 227° C.), which was recrystallized from 2-propanol.

Acetoacetic acid 3-(4,4-diphenylpiperidin-1-yl)propyl ester 23.6 g of 3-(4,4-diphenylpiperid-1-yl)-propanol were dissolved in 100 ml of absolute toluene, and 16 ml of a 50% strength solution of diketene in acetone were added with stirring. After standing for several days at room temperature (monitored by thin layer chromatography), the mixture was concentrated, and the residue was dried under high vacuum. The pale yellow, viscous oil which remains was employed without further purification for the nest stage.

2,6-Dimethyl-4-(4-nitrophenyl)-1,4-dihydropyridine-3,5-dicarboxy-ylic acid [3-(4,4-diphenylpiperidin-1-yl)propyl] ester methyl ester A solution of methyl 3-aminocrotonate (265 mg, 2.3 mmol, 1.0 equiv), 4-nitrobenzaldehyde (348 mg, 2.3 mmol, 1.0 equiv), and acetoacetic acid 3-[4,4-diphenylpiperidin-1-yl)propyl] ester (872 mg, 2.3 mmol, 1.0 equiv) in isopropanol was ref luxed under argon with stirring for 68 hours. Cooling and removal of solvent gave a residue, which was purified by flash chromatography (SiO₂, EtOAc-hexane, 1:1 and 1:2, followed by EtOAc) to afford 717 mg (51%) of yellow solid: ¹H NMR (300 MHz, CDCl₃) δ 1.73 (m, 2H), 2.22 (m, 2H), 2.30–2.51 (m, 8H), 2.34 (s, 3H), 2.35 (s, 3H), 3.63 (s, 3H), 4.05 (dt, J=2.1, 7.9 Hz, 2H), 5.06 (s, 1H), 5.73 (br s, 1H), 7.14 (m, 2H), 7.27 (m, 8H), 7.42 (dm, J=8.8 Hz, 2H), 8.06 (dm, J=8.8 Hz, 2H); ¹³C NMR (75 MHz, CDCl₃) δ 15.30, 19.65, 26.32, 36.11, 39.88, 44.60, 50.60, 51.12, 55.34, 62.66, 102.99, 107.55, 123.39, 125.67, 127.12, 128.33, 128.65, 144.80, 144.93, 146.36, 147.50, 154.78, 166.91, 167.43; IR (neat) 1698.0, 1684.7, 1517.5, 1345.7 cm$^{-1}$; CIMS (NH$_3$) 610 (M+1)$^+$, 553, 338.

2,6-Dimethyl-4-(4-nitrophenyl)-1,4-dihydropyridine-3,5-dicarboxylic acid |3-(4,4-diphenylpiperidin-1-yl)propyl| ester methyl ester hydrochloride (Compound 8)

To a solution of 2,6-dimethyl-4-(4-nitrophenyl)-1,4-dihydro-pyridine-3,5-dicarboxylic acid |3-(4,4-diphenylpiperidine-1-yl)-propyl| ester methyl ester (710 mg, 1.16 mmol, 1.0 equiv) in EtOH (5 mL) was added a solution of HCl in ether (1.0M, 1.5 mL, 1.5 mmol, 1.3 equiv). The solvents were removed and the residue was dissolved in CH$_2$Cl$_2$. This solution was added dropwise to 25 mL of ether to afford, after filtration, 500 mg of yellow crystalline solid: m.p. 152°–153° C. Anal. Calcd. for C$_{36}$H$_{39}$N$_3$O$_6$•HCl: C, 66.92; H, 6.24; N, 6.50. Found: C, 66.70; H, 5.99; N, 6.27

EXAMPLE 9

Protocol for the Determination of the Potency of α$_1$ Antagonists

The activity of compounds at the different human receptors was determined in vitro using cultured cell lines that selectively express the receptor of interest. These cell lines were prepared by transfecting the cloned CDNA or cloned genomic DNA or constructs containing both genomic DNA and CDNA encoding the human α-adrenergic, serotonin, histamine, and dopamine receptors as follows:

α$_{1A}$ Human Adrenergic Receptor

The entire coding region of α1A (1719 bp), including 150 basepairs of 5' untranslated sequence (5' UT) and 300 bp of 3' untranslated sequence (3' UT), was cloned into the BamHI and ClaI sites of the polylinker-modified eukaryotic expression vector pCEXV-3, called EXJ.HR. The construct involved the ligation of partial overlapping human lymphocyte genomic and hippocampal CDNA clones: 5' sequence were contained on a 1.2 kb SmaI-XhoI genomic fragment (the vector-derived BamHI site was used for subcloning instead of the internal insert-derived SmaI site) and 3' sequences were contained on an 1.3 kb XhoI-ClaI cDNA fragment (the ClaI site was from the vector polylinker). Stable cell lines were obtained by cotransfection with the plasmid α1A/EXJ (expression vector containing the α1A receptor gene) and the plasmid pGCcos3neo (plasmid containing the aminoglycoside transferase gene) into LM(tk$^-$), CHO, and NIH3T3 cells, using calcium phosphate technique. The cells were grown, in a controlled environment (37° C., 5% CO$_2$), as monolayers in Dulbecco's modified Eagle's Medium (GIBCO, Grand Island, N.Y.) containing 25 mM glucose and supplemented with 10% bovine calf serum, 100 units/ml penicillin g, and 100 µg/ml streptomycin sulfate. Stable clones were then selected for resistance to the antibiotic G-418 (1 mg/ml), and membranes were harvested and assayed for their ability to bind |$^3$H|prazosin as described below (see "Radioligand Binding assays").

α$_{1B}$ Human Adrenergic Receptor

The entire coding region of α1B (1563 bp), including 200 basepairs and 5' untranslated sequence (5' UT) and 600 bp of 3' untranslated sequence (3' UT), was cloned into the EcoRI site of pCEXV-3 eukaryotic expression vector. The construct involved ligating the full-length containing EcoRI brainstem cDNA fragment from λ ZapII into the expression vector. Stable cell lines were selected as described above.

α$_{1C}$ Human Adrenergic Receptor

The entire coding region of α1C (1401 bp), including 400 basepairs of 5' untranslated sequence (5' UT) and 200 bp of 3' untranslated sequence (3' UT), was cloned into the KpnI site of the polylinker-modified pCEXV-3-derived eukaryotic expression vector, EXJ.RH. The construct involved ligating three partial overlapping fragments: a 5' 0.6 kb HincII genomic clone, a central 1.8 EcoRI hippocampal cDNA clone, and a 3' 0.6 Kb PstI genomic clone. The hippocampal CDNA fragment overlaps with the 5' and 3' genomic clones so that the HincII and PstI sites at the 5' and 3' ends of the cDNA clone, respectively, were utilized for ligation. This full-length clone was cloned into the KpnI site of the expression vector, using the 5' and 3' KpnI sites of the fragment, derived from vector (i.e., pBluescript) and 3'-untranslated sequences, respectively. Stable cell lines were selected as described above.

Radioligand Binding Assays

Transfected cells from culture flasks were scraped into 5 ml of 5 mM Tris-HCl, 5 mM EDTA, pH 7.5, and lysed by sonication. The cell lysates were centrifuged at 1000 rpm for 5 min at 4° C., and the supernatant was centrifuged at 30,000×g for 20 min at 4° C. The pellet was suspended in 50 mM Tris-HCl, 1 mM MgCl$_2$, and 0.1% ascorbic acid at pH 7.5. Binding of the α$_1$ antagonist |$^3$H|prazosin (0.5 nM, specific activity 76.2 Ci/mmol) to membrane preparations of LM(tk$-$) cells seas done in a final volume of 0.25 ml and incubated at 37° C. for 20 min. Nonspecific binding was determined in the presence of 10 µM phentolamine. The reaction was stopped by filtration through GF/B filters using a cell harvester. Inhibition experiments, routinely consisting of 7 concentrations of the tested compounds, were analyzed using a non-linear regression curve-fitting computer program to obtain Ki values.

α$_2$ Human Adrenergic Receptors

To determine the potency of α$_1$ antagonists at the α$_2$ receptors, LM(tk$-$) cell lines stably transfected with the genes encoding the α$_{2A}$, α$_{2B}$, and α$_{2C}$ receptors were used. The cell line expressing the α$_{2A}$ receptor is designated L-α$_{2A}$, and was deposited on Nov. 6, 1992 under ATCC Accession No. CRL 11180. The cell line expressing the α$_{2B}$ receptor is designated L-NGC-α$_{2B}$, and was deposited on Oct. 25, 1989 under ATCC Accession No. CRL10275. The cell line expressing the α$_{2C}$ receptor is designated L-α$_{2C}$, and was deposited on Nov. 6, 1992 under ATCC Accession No. CRL-11181. Cell lysates were prepared as described above (see Radioligand Binding Assays), and suspended in 25 mM glycylglycine buffer (pH 7.6 at room temperature). Equilibrium competition binding assay were performed using |3H|rauwolscine (0.5 nM), and nonspecific binding was determined by incubation with 10 µM phentolamine. The bound radioligand was separated by filtration through GF/B filters using a cell harvester.

Human Histamine H$_1$ Receptor

The coding sequence of the human histamine H$_1$ receptor, homologous to the bovine H$_1$ receptor, was obtained from a human hippocampal cDNA library, and was cloned into the eukaryotic expression vector pCEXV-3. The plasmid DNA for the H$_1$ receptor is designated pcEXV-H$_1$, and was deposited on Nov. 6, 1992 under ATCC Accession No. 75346. This construct was transfected into COS-7 cells by the DEAE-dextran method. Cells were harvested after 72 hours and lysed by sonication in 5 mM Tris-HCl, 5 mM EDTA, pH 7.5. The cell lysates were centrifuged at 1000 rpm for 5 min at 4° C., and the supernatant was centrifuged at 30,000×g for 20 min. at 4° C. The pellet was suspended in 37.8 mM NaHPO$_4$, 12.2 mM KH$_2$PO$_4$, pH 7.5. The binding of the histamine H$_1$ antagonist |$^3$H|mepyramine (1 nM, specific activity: 24.8 Ci/mM) was done in a final volume of 0.25 ml and incubated at room temperature for 60 min. Nonspecific binding was determined in the presence of 10 µM mepyramine. The bound radioligand was separated by filtration through GF/B filters using a cell harvester.

Human Histamine H$_2$ Receptor

The coding sequence of the human H$_2$ receptor was obtained from a human placenta genomic library, and cloned into the cloning site of PCEXV-3 eukaryotic expression vector. The plasmid DNA for the $H_2$ receptor is designated pcEXV-$H_2$, and was deposited on Nov. 6, 1992 under ATCC Accession No. 75345.

This construct was transfected into COS-7 cells by the DEAE-dextran method. Cells were harvested after 72 hours and lysed by sonication in 5 mM Tris-HCl, 5 mM EDTA, pH 7.5. The cell lysates were centrifuged at 1000 rpm for 5 min at 4° C., and the supernatant was centrifuged at 30,000×g for 20 min at 4° C. The pellet was suspended in 37.8 mM NaHPO$_4$, 12.2 mM K2PO$_4$, pH 7.5. The binding of the histamine $H_2$ antagonist $|^3H|$tiotidine (5 nM, specific activity: 70 Ci/mM) was done in a final volume of 0.25 ml and incubated at room temperature for 60 min. Nonspecific binding was determined in the presence of 10 µM histamine. The bound radioligand was separated by filtration through GF/B filters using a cell harvester.

Human Serotonin Receptors $5HT_{1D\alpha}$, $5HT_{1D\beta}$, $5HT_{1E}$, $5HT_{1F}$ Receptors The cell lysates of LM(tk−) clonal cell line stably transfected with the genes encoding each of these 5HT receptor-subtypes were prepared as described above. The cell line for the $5HT_{1D\alpha}$ receptor, designated as Ltk-8-30-84, was deposited on Apr. 17, 1990, and accorded ATCC Accession No. CRL 10421. The cell for the $5HT_{1D\beta}$ receptor, designated as Ltk-11, was deposited on Apr. 17, 1990, and accorded ATCC Accession No. CRL 10422. The cell line for the $5H_{1E}$ receptor, designated 5-$HT_{1E}$-7, was deposited on Nov. 6, 1991, and accorded ATCC Accession No. CRL 10913. The cell line for the 5HT1F receptor, designated L-5-$HT_{1F}$, was deposited on Dec. 27, 1991, and accorded ATCC Accession No. ATCC 10957. These preparations were suspended in 50 mM Tris-HCl buffer (pH 7.4 at 37° C.) containing 10 mM MgCl$_2$, 0.2 mM EDTA, 10 µM pargyline, and 0.1% ascorbate. The potency of $\alpha_1$ antagonists was determined in competition binding assay by incubation for 30 minutes at 37° C. in the presence of 5 nM $|3H|$serotonin. Nonspecific binding was determined in the presence of 10 µM serotonin. The bound radioligand was separated by filtration through GF/B filters using a cell harvester.

Human $5HT_2$ Receptor

The coding sequence of the human $5HT_2$ receptor was obtained from a human brain cortex cDNA library, and cloned into the cloning site of pCEXV-3 eukaryotic expression vector. This construct was transfected into COS-7 cells by the DEAE-dextran method. Cells were harvested after 72 hours and lysed by sonication in 5 mM Tris-HCl, 5 mM EDTA, pH 7.5. This cell line was deposited with the ATCC on Oct. 31, 1989, designated as L-NGC-5$HT_2$, and was accorded ATCC Accession No. CRL 10287. The cell lysates were centrifuged at 1000 rpm for 5 minutes at 4° C., and the supernatant was centrifuged at 30,000×g for 20 minutes at 4° C. The pellet was suspended in 50 mM Tris-HCl buffer (pH 7.7 at room temperature) containing 10 mM MgSO$_4$, 0.5 mM EDTA, and 0.1% ascorbate. The potency of $\alpha_1$ antagonists at $5HT_2$ receptors was determined in equilibrium competition binding assays using $|3H|$ketanserin (1 nM). Nonspecific binding was defined by the addition of 10 µM mianserin. The bound radioligand was separated by filtration through GF/B filters using a cell harvester.

Human Dopamine $D_2$ Receptors

The potency of $\alpha_1$ antagonists at the D2 receptor was determined using membrane preparations from COS-7 cells transfected with the gene encoding the human $D_2$ receptor. The coding region for the human D2 receptor was obtained from a human striatum cDNA library, and cloned into the cloning site of PCDNA 1 eukariotic expression vector. The plasmid DNA for the $D_2$ receptor is designated pcEXV-D2, and was deposited on Nov. 6, 1992 under ATCC Accession No. 75344. This construct was transfected into COS-7 cells by the DEAE-dextran method. Cells were harvested after 72 hours and lysed by sonication in 5 nM Tris-HCl, 5 mM EDTA, pH 7.5. The cell lysates were centrifuged at 1000 rpm for 5 minutes at 4° C., and the supernatant was centrifuged at 30,000×g for 20 minutes at 4° C. The pellet was suspended in 50 mM Tris-HCl (pH 7.4) containing 1 mM EDTA, 5 mM KCl, 1.5 mM CaCl$_2$, 4 mM MgCl$_2$, and 0.1% ascorbic acid. The cell lysates were incubated with $|3H|$spiperone (2 nM), using 10 µM (+)Butaclamol to determine nonspecific binding.

Other Dopamine receptors are prepared by known methods (D$_3$: Sokoloff, P. et al., Nature, 347, 146 (1990), and deposited with the European Molecular Biologicel Laboratory (EMBL) Genbank as X53944; D$_4$: Van Tol, H. H. M., et al., Nature, 350, 610 (1991), and deposited with EMBL Genbank as X58497; D$_5$: Sunahara, R. K., et al., Nature, 350, 614 (1991), and deposited with EMBL Genbank as X58454-HU HD 5DR).

Determination of the Activity of $\alpha_1$ Antagonists at Calcium Channels

The potency of $\alpha_1$ antagonists at calcium channels was determined in competition binding assays of $|3H|$ nitrendipine to membrane fragments of rat cardiac muscle, essentially as described by Glossman and Ferry (Methods in Enzymology 109:513–550, 1985). Briefly, the tissue was minced and homogenized in 50 mM Tris-HCl (pH 7.4) containing 0.1 mM phenylmethylsulfonyl fluoride. The homogenates were centrifuged at 1000 g for 15 minutes, the resulting supernatant was centrifuged at 45,000 g for 15 minutes. The 45,000 g pellet was suspended in buffer and centrifuged a second time. Aliquots of membrane protein were incubated for 30 minutes at 37° C. in the presence of $|3H|$nitrendipine (1 nM), and nonspecific binding was determined in the presence of 10 µM nifedipine. The bound radioligand was separated by filtration through GF/B filters using a cell harvester.

EXAMPLE 10

Functional Properties of $\alpha_1$ Antagonists in the Human Prostate

The efficacy of $\alpha_1$ adrenergic antagonists for the treatment of benign prostatic hyperplasia (BPH) is related to their ability to elicit relaxation of prostate smooth muscle. An index of this efficacy can be obtained by determining the potency of $\alpha_1$ antagonists to antagonize the contraction of human prostatic tissue induced by an $\alpha_1$ agonist "in vitro". Furthermore, by comparing the potency of subtype selective $\alpha_1$ antagonists in binding assays using human $\alpha_1$ receptors with their potency to inhibit agonist-induced smooth muscle contraction, it is possible to determine which of the $\alpha_1$ adrenergic receptor subtypes is involved in the contraction of prostate smooth muscle.

Methods

Prostatic adenomas were obtained at the time of surgery from patients with symptomatic BPH. These were cut into longitudinal strips of 15 mm long and 2–4 mm wide, and suspended in 5 ml organ baths containing Krebs buffer (pH 7.4). The baths were maintained at 37° C. and continuously oxygenated with 5% $CO_2$ and 95% $O_2$. Isometric tension was measured with a Grass Instrument FT03 force transducer interfaced with a computer. Tissue strips were contracted with varying concentrations of phenylephrine after incubating for 20 minutes in the absence and presence of at least three different concentrations of antagonist. Dose-response curves for phenylephrine were constructed, and the antagonist potency (pA$_2$) was estimated by the dose-ratio method. The concentration of some antagonists in the tissue bath was assessed by measuring the displacement of $|3H|$ prazosin by aliquots of the bath medium, using membrane preparations of the cloned human $\alpha_{1C}$ receptor. This control was necessary to account for losses of antagonist due to adsorption to the tissue bath and/or metabolism during the time the antagonists were equilibrated with the prostate tissue.

Results

Figure 2A:
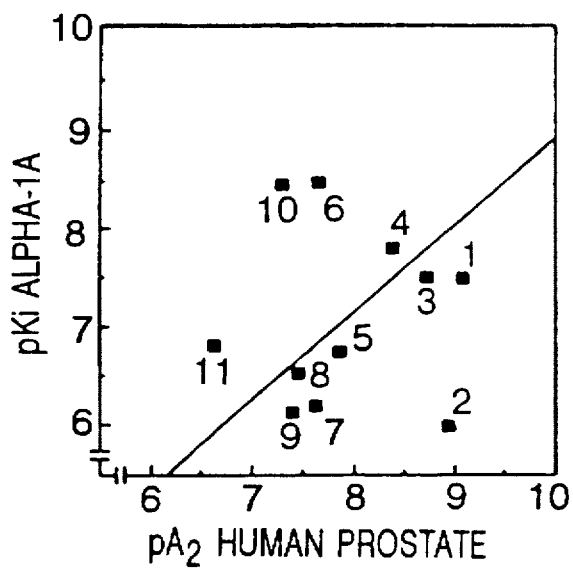
FIGS. 2A–2C illustrate the correlation of inhibition constants ($pK_i$) for a series of $\alpha_1$ antagonists at the cloned human $\alpha_{1A}$, $\alpha_{1B}$, and $\alpha_{1C}$ receptors with efficiency of blocking contraction of human prostate tissue ($pA_2$).
Figure 2B:
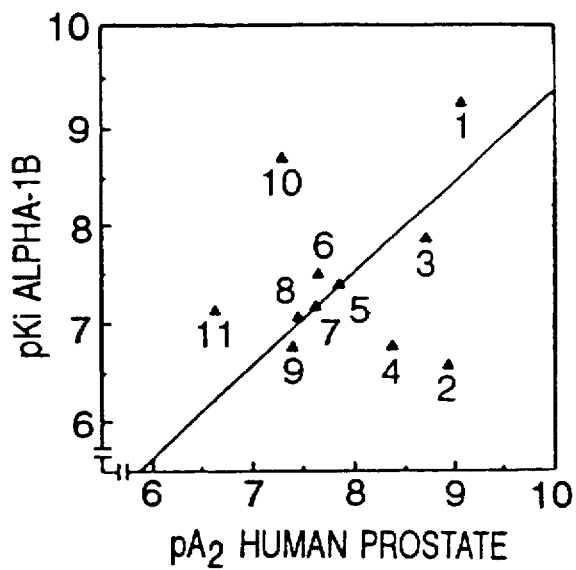
Figure 2C:
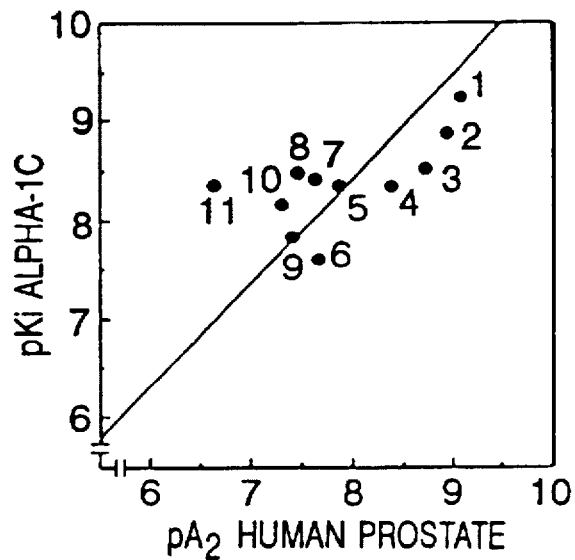

Table 1 shows that the $pA_2$ values measured for a series of $\alpha_1$ antagonists in human prostate tissue correlate closely (r=0.76) with the corresponding $pK_i$ values measured in the $\alpha_{1C}$ receptor assays. In contrast, the human prostate $pA_2$ values correlate poorly with the $pK_i$ values measured at the $\alpha_{1A}$ (r=-0.06) and $\alpha_{1B}$ (r=-0.24) adrenergic receptors. (See FIGS. 2A-2C.) Thus, antagonists which are more potent at blocking the $\alpha_{1C}$ adrenergic receptor are more effective at blocking the contraction of the human prostate than antagonists which are more potent at the $\alpha_{1A}$ or $\alpha_{1B}$ adrenergic receptors. In addition, antagonists which are selective for the $\alpha_{1C}$ receptor will have a better therapeutic ratio than nonselective $\alpha$ antagonists.

With Compound 11, the low $pA_2$ observed in the prostate may be attributed to tissue absorption or metabolism.

Table 2 illustrates the cross reactivity of $\alpha_1$ antagonists at other receptors such as $\alpha_{2A}$, $\alpha_{2B}$, $\alpha_{2C}$, histamine $H_1$, $H_2$, serotonin 5-$HT_{1D\alpha}$, 5-$HT_{1D\beta}$, 5-$HT_{1E}$, 5-$HT_{1F}$, 5-$HT_2$, and dopamine $D_2$. Only compounds 11, 8 and 2 have binding affinities which are greater than ten-fold higher at $\alpha_{1C}$ receptors than the binding affinities at other receptors.

TABLE 1

COMPARISON OF THE BINDING POTENCY ($pK_i$) OF ALPHA-1 ANTAGONISTS IN CLONED HUMAN RECEPTORS AND THEIR PROTENCY ($pA_2$) TO INHIBIT PROSTATE SMOOTH MUSCLE CONTRACTION

| Compound | Human Alpha-1 Adrenergic ($pK_i$) | | | Human Prostate (pA) |
|---|---|---|---|---|
| | $\alpha 1A$ | $\alpha 1B$ | $\alpha 1C$ | |
| 1 Prazosin | 9.48 | 9.26 | 9.23 | 9.08 |
| 2 Compound 2 | 5.98 | 6.57 | 8.87 | 8.94 |
| 3 A-30360 | 7.49 | 7.86 | 8.52 | 8.72 |
| 4 5-Methyl-Urapidil | 7.79 | 6.77 | 8.35 | 8.38 |
| 5 Indoramin | 6.74 | 7.39 | 8.35 | 7.86 |
| 6 SKF-104856 | 8.48 | 7.50 | 7.60 | 7.66 |
| 7 Compound 7 | 6.82 | 7.18 | 8.42 | 7.63 |
| 8 Compound 8 | 6.52 | 7.07 | 8.48 | 7.46 |
| 9 Compound 9 | 6.12 | 6.76 | 7.83 | 7.41 |
| 10 Terazosin | 8.46 | 8.71 | 8.16 | 7.30 |
| 11 Compound 11 | 6.81 | 7.14 | 8.36 | 6.64 |

What is claimed is:

1. A method of treating benign prostatic hyperplasia in a subject which comprises administering to the subject a therapeutically effective amount of an antagonist which binds to a human $\alpha_{1C}$ adrenergic receptor with a binding affinity at least 48-fold higher than the binding affinity with which the antagonist binds to a human $\alpha_{1B}$ adrenergic receptor.

2. The method of claim 1, wherein the binding affinity of the antagonist is at least 10-fold higher for the human $\alpha_{1C}$ adrenergic receptor than it is for a human $\alpha_{1A}$ adrenergic receptor or a human $\alpha_2$ adrenergic receptor.

3. The method of claim 1, wherein the binding affinity of the antagonist is at least 10-fold higher for the human $\alpha_{1C}$ adrenergic receptor than it is for a human histamine $H_1$ receptor.

4. The method of claim 1, wherein the binding affinity of the antagonist is at least 10-fold higher for the human $\alpha_{1C}$ adrenergic receptor than it is for a calcium channel.

5. The method of claim 1, wherein the binding affinity of the antagonist is at least 10-fold higher for the human $\alpha_{1C}$ adrenergic receptor than it is for a human dopamine $D_2$ receptor.

6. The method of claim 1, wherein the binding affinity of the antagonist is at least 10-fold higher for the human $\alpha_{1C}$ adrenergic receptor than it is for a human serotonin receptor.

7. The method of claim 1, wherein the binding affinity of the antagonist is at least 10-fold higher for the human $\alpha_{1C}$ adrenergic receptor than it is for a human dopamine $D_3$, $D_4$, or $D_5$ receptor.

8. The method of claim 1, wherein the binding affinity of the antagonist is at least 200-fold higher for the human $\alpha_{1C}$ adrenergic receptor than it is for the human $\alpha_{1B}$ adrenergic receptor.

9. The method of claim 8, wherein the binding affinity of the antagonist is at least 51-fold higher for the human $\alpha_{1C}$ adrenergic receptor than it is for the human histamine $H_1$ receptor.

10. A method of treating benign prostatic hyperplasia in a subject which comprises administering to the subject a therapeutically effective amount of an antagonist which binds to a human $\alpha_{1C}$ adrenergic receptor with a binding affinity at least 26-fold higher than the binding affinity with which the antagonist binds to a human $\alpha_{1B}$ adrenergic receptor.

TABLE 2

CROSS REACTIVITY OF $\alpha_1$ ANTAGONISTS AT CLONED HUMAN RECEPTORS ($pK_i$)

| Compound | $\alpha_1$ Adrenergic | | | $\alpha_2$ Adrenergic | | | Histamine | | Serotonin | | | | | Dopamine | Calcium |
|---|---|---|---|---|---|---|---|---|---|---|---|---|---|---|---|
| | $\alpha 1A$ | $\alpha 1B$ | $\alpha 1C$ | $\alpha 2a$ | a2b | $\alpha 2c$ | H1 | H2 | 5HT1D$\alpha$ | 5HT1DB | 5HT1E | 5HT1F | 5HT2 | D2 | Channel |
| Terezosin | 8.46 | 8.71 | 8.16 | 6.26 | 7.51 | 6.64 | 4.00 | 5.04 | <6.0 | <6.0 | <5.0 | <5.0 | <5.0 | <5.0 | 5.19 |
| Prezosin | 9.48 | 9.26 | 9.23 | 6.76 | 7.64 | 7.65 | 4.00 | 5.19 | <5.0 | <5.0 | ND | ND | <6.0 | <5.0 | 4.57 |
| 5-Methylurepidil | 7.79 | 6.77 | 8.35 | 6.63 | 7.38 | 6.88 | 5.16 | 4.47 | 7.30 | 6.82 | ND | ND | <6.0 | <5.0 | ND |
| Indormin | 6.74 | 7.39 | 8.35 | 4.94 | 5.72 | 5.22 | 7.37 | 5.63 | <6.0 | <6.0 | <5.0 | <5.0 | <7.0 | <8.0 | 4.53 |
| Compound 11 | 6.81 | 7.14 | 8.36 | 6.86 | 6.90 | 6.92 | 5.14 | 7.45 | <6.0 | <6.0 | <5.0 | <5.0 | <7.0 | <6.0 | 5.18 |
| A-30360 | 7.49 | 7.86 | 8.52 | 6.69 | 6.37 | 6.23 | 6.03 | 5.77 | <6.0 | <6.0 | <5.0 | <5.0 | <8.0 | <9.0 | 5.26 |
| Compound 7 | 6.82 | 7.18 | 8.42 | 6.19 | 6.07 | 6.09 | 7.59 | 6.02 | <6.0 | <5.0 | <5.9 | <5.0 | <6.0 | <7.0 | 4.79 |
| Compound 9 | 6.12 | 6.76 | 7.83 | 5.80 | 5.69 | 5.90 | 7.29 | 5.44 | <6.0 | <6.0 | <5.0 | <5.0 | <7.0 | <7.0 | 4.44 |
| SKF-104856 | 8.48 | 7.50 | 7.60 | 7.30 | 8.49 | 7.60 | 5.59 | 5.84 | <7.0 | <7.0 | <6.0 | <7.0 | <6.0 | <7.0 | 4.68 |
| S-Niguldipine | 6.72 | 7.07 | 8.75 | 6.19 | 5.24 | 6.43 | 6.78 | 6.24 | ND | ND | ND | ND | <7.0 | <7.0 | 8.04 |
| Compound 8 | 6.52 | 7.07 | 8.48 | 5.99 | 6.12 | 5.77 | 6.67 | 6.11 | <6.0 | <5.0 | <5.0 | <5.0 | <7.0 | <6.0 | 6.87 |
| Compound 2 | 5.98 | 6.57 | 8.87 | 5.48 | 5.93 | 5.88 | 7.16 | 7.48 | <7.0 | <6.0 | <5.0 | <5.0 | <6.0 | <7.0 | 6.13 |

ND = Not Determined

11. The method of claim 3, wherein the binding affinity of the antagonist is at least 65-fold higher for the human $\alpha_{1C}$ adrenergic receptor than it is for the human histamine $H_1$ receptor.

12. The method of claim 3, wherein the binding affinity of the antagonist is at least 93-fold higher for the human $\alpha_{1C}$ adrenergic receptor than it is for the human histamine $H_1$ receptor.

13. A method of treating benign prostatic hyperplasia in a subject which comprises administering to the subject a therapeutically effective amount of an antagonist which binds to a human $\alpha_{1C}$ adrenergic receptor with a binding affinity at least 35-fold higher than the binding affinity with which the antagonist binds to a human $\alpha_{1A}$ adrenergic receptor and at least 417-fold higher than it is for a human histamine $H_1$ receptor.

14. The method of claim 10, wherein the binding affinity of the antagonist is at least 91-fold higher for the human $\alpha_{1C}$ adrenergic receptor than it is for the human $\alpha_{1A}$ adrenergic.

15. The method of claim 2, wherein the binding affinity of the antagonist is at least 107-fold higher for the human $\alpha_{1C}$ adrenergic receptor than it is for the human $\alpha_{1A}$ adrenergic receptor.

16. The method of claim 8, wherein the binding affinity of the antagonist is at least 776-fold higher for the human $\alpha_{1C}$ adrenergic receptor than it is for the human $\alpha_{1A}$ adrenergic receptor.

17. The method of claim 3, wherein the binding affinity of the antagonist is at least 28-fold higher than it is for a human $\alpha_2$ adrenergic receptor.

18. The method of claim 10, wherein the binding affinity of the antagonist for the human $\alpha_{1C}$ adrenergic receptor is (i) at least 91-fold higher than it is for the human $\alpha_{1A}$ adrenergic receptor, (ii) at least 65-fold higher than it is for the human histamine $H_1$ receptor, and (iii) at least 229-fold higher than it is for the human $\alpha_2$ adrenergic receptor.

19. The method of claim 1, wherein the binding affinity of the antagonist for the human $\alpha_{1C}$ adrenergic receptor is (i) at least 107-fold higher than it is for the human $\alpha_{1A}$ adrenergic receptor, (ii) at least 93-fold higher than it is for the human histamine $H_1$ receptor, and (iii) at least 209-fold higher than it is for the human $\alpha_2$ adrenergic receptor.

20. The method of claim 1, wherein the binding affinity of the antagonist for the human $\alpha_{1C}$ adrenergic receptor is (i) at least 776-fold higher than it is for the human $\alpha_{1A}$ adrenergic receptor, (ii) at least 200-fold higher than it is for the human $\alpha_{1B}$ adrenergic receptor, (iii) at least 51-fold higher than it is for the human histamine $H_1$ receptor, and (iv) at least 871-fold higher than it is for the human $\alpha_2$ adrenergic receptor.

21. The method of claim 10, wherein the binding affinity of the antagonist for the human $\alpha_{1C}$ adrenergic receptor is at least 41-fold higher than it is for the calcium channel.

22. The method of claim 8, wherein the binding affinity of the antagonist for the human $\alpha_{1C}$ adrenergic receptor is at least 550-fold higher than it is for the calcium channel.

23. The method of claim 8, wherein the binding affinity of the antagonist for the human $\alpha_{1C}$ adrenergic receptor is at least 25-fold higher than it is for a human histamine $H_2$ receptor.

24. The method of claim 10, wherein the binding affinity of the antagonist for the human $\alpha_{1C}$ adrenergic receptor is at least 234-fold higher than it is for a human histamine $H_2$ receptor.

25. The method of claim 3, wherein the binding affinity of the antagonist for the human $\alpha_{1C}$ adrenergic receptor is at least 324-fold higher than it is for a human histamine $H_2$ receptor.

26. The method of claim 10, wherein the binding affinity of the antagonist for the human $\alpha_{1C}$ adrenergic receptor is at least 30-fold higher than it is for the human serotonin receptor.

27. The method of claim 6, wherein the binding affinity of the antagonist for the human $\alpha_{1C}$ adrenergic receptor is at least 56-fold higher than it is for the human serotonin receptor.

28. The method of claim 8, wherein the binding affinity of the antagonist for the human $\alpha_{1C}$ adrenergic receptor is at least 74-fold higher than it is for the human serotonin receptor.

29. A method of inhibiting contraction of prostatic tissue which comprises contacting the prostate tissue with an effective contraction-inhibiting amount of an antagonist which binds to a human $\alpha_{1C}$ adrenergic receptor with a binding affinity at least 48-fold higher than the binding affinity with which the antagonist binds to a human $\alpha_{1B}$ adrenergic receptor.

30. The method of claim 29, wherein the binding affinity of the antagonist is at least 10-fold higher for the human $\alpha_{1C}$ adrenergic receptor than it is for a human $\alpha_{1A}$ adrenergic receptor or a human $\alpha_2$ adrenergic receptor.

31. The method of claim 29, wherein the binding affinity of the antagonist is at least 10-fold higher for the human $\alpha_{1C}$ adrenergic receptor than it is for a human histamine $H_1$ receptor.

32. The method of claim 29, wherein the binding affinity of the antagonist is at least 10-fold higher for the human $\alpha_{1C}$ adrenergic receptor than it is for a calcium channel.

33. The method of claim 29, wherein the binding affinity of the antagonist is at least 10-fold higher for the human $\alpha_{1C}$ adrenergic receptor than it is for a human dopamine $D_2$ receptor.

34. The method of claim 29, wherein the binding affinity of the antagonist is at least 10-fold higher for the human $\alpha_{1C}$ adrenergic receptor than it is for a human serotonin receptor.

35. The method of claim 29, wherein the binding affinity of the antagonist is at least 10-fold higher for the human $\alpha_{1C}$ adrenergic receptor than it is for a human dopamine $D_3$, $D_4$, or $D_5$ receptor.

36. The method of claim 29, wherein the binding affinity of the antagonist is at least 200-fold higher for the human $\alpha_{1C}$ adrenergic receptor than it is for the human $\alpha_{1B}$ adrenergic receptor.

37. The method of claim 36, wherein the binding affinity of the antagonist is at least 51-fold higher for the human $\alpha_{1C}$ adrenergic receptor than it is for the human histamine $H_1$ receptor.

38. A method of inhibiting contraction of prostatic tissue which comprises contacting the prostate tissue with an effective contraction-inhibiting amount of an antagonist which binds to a human $\alpha_{1C}$ adrenergic receptor with a binding affinity at least 26-fold higher than the binding affinity with which the antagonist binds to a human $\alpha_{1B}$ adrenergic receptor.

39. The method of claim 38, wherein the binding affinity of the antagonist is at least 65-fold higher for the human $\alpha_{1C}$ adrenergic receptor than it is for the human histamine $H_1$ receptor.

40. The method of claim 31, wherein the binding affinity of the antagonist is at least 93-fold higher for the human $\alpha_{1C}$ adrenergic receptor than it is for the human histamine $H_1$ receptor.

41. A method of inhibiting contraction of prostatic tissue which comprises contacting the prostate tissue with an effective contraction-inhibiting amount of an antagonist which binds to a human $\alpha_{1C}$ adrenergic receptor with a binding affinity at least 35-fold higher than it is for a human $\alpha_{1A}$ adrenergic receptor and at least 417-fold higher than it is for a human histamine $H_1$ receptor.

42. The method of claim 38, wherein the binding affinity of the antagonist is at least 91-fold higher for the human $\alpha_{1C}$ adrenergic receptor than it is for the human $\alpha_{1A}$ adrenergic receptor.

43. The method of claim 30, wherein the binding affinity of the antagonist is at least 107-fold higher for the human $\alpha_{1C}$ adrenergic receptor than it is for the human $\alpha_{1A}$ adrenergic receptor.

44. The method of claim 36, wherein the binding affinity of the antagonist is at least 776-fold higher for the human $\alpha_{1C}$ adrenergic receptor than it is for the human $\alpha_{1A}$ adrenergic receptor.

45. The method of claim 41, wherein the binding affinity of the antagonist is at least 28-fold higher than it is for a human $\alpha_2$ adrenergic receptor.

46. The method of claim 38, wherein the binding affinity of the antagonist for the human $\alpha_{1C}$ adrenergic receptor is (i) at least 91-fold higher than it is for the human $\alpha_{1A}$ adrenergic receptor, (ii) at least 65-fold higher than it is for the human histamine $H_1$ receptor, and (iii) at least 229-fold higher than it is for the human $\alpha_2$ adrenergic receptor.

47. The method of claim 29, wherein the binding affinity of the antagonist for the human $\alpha_{1C}$ adrenergic receptor is (i) at least 107-fold higher than it is for the human $\alpha_{1A}$ adrenergic receptor, (ii) at least 93-fold higher than it is for the human histamine $H_1$ receptor, and (iii) at least 209-fold higher than it is for the human $\alpha_2$ adrenergic receptor.

48. The method of claim 29, wherein the binding affinity of the antagonist for the human $\alpha_{1C}$ adrenergic receptor is (i) at least 776-fold higher than it is for the human $\alpha_{1A}$ adrenergic receptor, (ii) at least 200-fold higher than it is for the human $\alpha_{1B}$ adrenergic receptor, (iii) at least 51-fold higher than it is for the human histamine $H_1$ receptor, and (iv) at least 871-fold higher than it is for the human $\alpha_2$ adrenergic receptor.

49. The method of claim 38, wherein the binding affinity of the antagonist for the human $\alpha_{1C}$ adrenergic receptor is at least 41-fold higher than it is for the calcium channel.

50. The method of claim 36, wherein the binding affinity of the antagonist for the human $\alpha_{1C}$ adrenergic receptor is at least 550-fold higher than it is for the calcium channel.

51. The method of claim 36, wherein the binding affinity of the antagonist for the human $\alpha_{1C}$ adrenergic receptor is at least 25-fold higher than it is for a human histamine $H_2$ receptor.

52. The method of claim 38, wherein the binding affinity of the antagonist for the human $\alpha_{1C}$ adrenergic receptor is at least 234-fold higher than it is for a human histamine $H_2$ receptor.

53. The method of claim 31, wherein the binding affinity of the antagonist for the human $\alpha_{1C}$ adrenergic receptor is at least 324-fold higher than it is for a human histamine $H_2$ receptor.

54. The method of claim 38, wherein the binding affinity of the antagonist for the human $\alpha_{1C}$ adrenergic receptor is at least 30-fold higher than it is for the human serotonin receptor.

55. The method of claim 34, wherein the binding affinity of the antagonist for the human $\alpha_{1C}$ adrenergic receptor is at least 56-fold higher than it is for the human serotonin receptor.

56. The method of claim 36, wherein the binding affinity of the antagonist for the human $\alpha_{1C}$ adrenergic receptor is at least 74-fold higher than it is for the human serotonin receptor.

* * * * *

UNITED STATES PATENT AND TRADEMARK OFFICE
CERTIFICATE OF CORRECTION

PATENT NO. : 5,780,485
DATED : July 14, 1998
INVENTOR(S) : Charles Gluchowski, Carlos C. Forray, George Chiu, Theresa A. Branchek, John M. Wetzel, Paul R. Hartig It is certified that error appears in the above-identified patent and that said Letters Patent is hereby corrected as shown below:

column 7, line 27: "$Na_2CO_3$" should read --$Na_2CO_3$--
        line 64: "-benzamidopiperidi.ne" should read ---benzamidopiperidine--
column 8, line 8: "143°-144°O.C;" should read --143°-144° C--
        line 28: "$C_{22}H_{25}ClN_2I_2 \cdot HCl \cdot H_2O$" should read --$C_{22}H_{25}ClN_2O_2 \cdot HCl \cdot H_2O$--
column 9, line 32: "ref luxed" should read --refluxed-
        line 42: "-methylthisno" should read ---methylthieno--
column 10, line 35: "$Na_2SO_4$" should read --$Na_2SO_4$--
column 12, line 25: "$CH_{40}N_4O_5 \cdot HCl \cdot H_2O$:" should read --$C_{36}H_{40}N_4O_5 \cdot HCl \cdot H_2O$
        line 58: "ref luxed" should read --refluxed--
column 14, line 19: "seas" should read --was--
column 15, line 41: "COS-7 cells" should read --LM(tk-) cells--
column 17-18, table 2, line 4: "5HTZ" should read --5HT2--
        table 2, line 5: "Terezosin" should read --Terazosin--
        table 2, line 6: "Prezosin" should read --Prazosin--
        table 2, line 7: "5-Methylurepidil" should read --5-Methylurapidil--
        table 2, line 8: "Indormin" should read --Indoramin--
        table 2, line 9: "5.14" should read --5.74--
        table 2, line 11: "<5.9" should read --<5.0--

UNITED STATES PATENT AND TRADEMARK OFFICE
CERTIFICATE OF CORRECTION

PATENT NO.  : 5,780,485
DATED       : July 14, 1998
INVENTOR(S) : Charles Gluchowski, et al It is certified that error appears in the above-identified patent and that said Letters Patent is hereby corrected as shown below:

column 19, claim 17, line 27: "claim 3" should read --claim 13--

Signed and Sealed this

Second Day of March, 1999

Attest:

Attesting Officer

Q. TODD DICKINSON

Acting Commissioner of Patents and Trademarks